US009474447B2

(12) United States Patent
Schmidtlin et al.

(10) Patent No.: US 9,474,447 B2
(45) Date of Patent: Oct. 25, 2016

(54) ANAMORPHIC LENS FOR ROTATIONAL SCANNING SURGICAL LASER PROBE

(71) Applicant: Alcon Research, Ltd., Fort Worth, TX (US)

(72) Inventors: Edouard G. Schmidtlin, Studio City, CA (US); Tammo Heeren, Aliso Viejo, CA (US)

(73) Assignee: NOVARTIS AG, Basel (CH)

( * ) Notice: Subject to any disclaimer, the term of this patent is extended or adjusted under 35 U.S.C. 154(b) by 590 days.

(21) Appl. No.: 13/848,228

(22) Filed: Mar. 21, 2013

(65) Prior Publication Data

US 2014/0288417 A1   Sep. 25, 2014

(51) Int. Cl.
*A61B 5/00* (2006.01)
*A61B 3/00* (2006.01)
*A61F 9/008* (2006.01)

(52) U.S. Cl.
CPC ............ *A61B 5/0066* (2013.01); *A61B 3/0008* (2013.01); *A61F 9/008* (2013.01); *A61F 2009/00851* (2013.01)

(58) Field of Classification Search
CPC .............. A61B 5/0066; A61B 3/0008; A61B 3/102–3/112; A61B 2090/3735; A61F 2009/00851; G02B 13/08–13/12
See application file for complete search history.

(56) References Cited

U.S. PATENT DOCUMENTS

| | | | | |
|---|---|---|---|---|
| 4,362,367 A | * | 12/1982 | Hammer ................. | G02B 13/08 359/710 |
| 5,423,798 A | * | 6/1995 | Crow ...................... | A61F 9/008 606/10 |
| 6,160,826 A | * | 12/2000 | Swanson ............. | A61B 1/00183 372/102 |
| 6,219,169 B1 | * | 4/2001 | Iizuka .................... | G02B 13/10 359/234 |
| 2007/0081257 A1 | | 4/2007 | Bowron et al. | |
| 2011/0178409 A1 | * | 7/2011 | Harris .................. | A61B 5/0066 600/476 |
| 2012/0245569 A1 | | 9/2012 | Papac et al. | |
| 2012/0330101 A1 | | 12/2012 | Brennan et al. | |
| 2013/0022345 A1 | * | 1/2013 | Dodoc .................. | G02B 13/08 396/439 |

OTHER PUBLICATIONS

PCT International Search Report for corresponding International Application No. PCT/US2014/031158 with mailing date Aug. 28, 2014, 2 pages.
Ren, Jian, "Ex Vivo Optical Coherence Tomography Imaging of Collector Channels with a Scanning Endoscopic Probe", IOVS, vol. 52, No. 7, pp. 3921-3925, 2011.

* cited by examiner

*Primary Examiner* — Serkan Akar
(74) *Attorney, Agent, or Firm* — Jason Finch (57) ABSTRACT

A surgical probe can include an outer cannula; an inner cannula, rotatably disposed inside the outer cannula; a rotational scanner, disposed at an end of the inner cannula and configured to receive a light beam from a delivery fiber and to scan the light beam along a loop; and an anamorphic optical element, disposed at an end of the outer cannula and configured to receive the light beam scanned along the loop and to output the light beam along an anisotropically compressed loop. A corresponding method can include providing a light beam by a light source; coupling the light beam to a rotational scanner at an end of an inner cannula; scanning the light beam by the rotational scanner along a loop; and receiving the light beam scanned along the loop by an anamorphic optical element and outputting the light beam along an anisotropically compressed loop to a target.

17 Claims, 10 Drawing Sheets

ANAMORPHIC LENS FOR ROTATIONAL SCANNING SURGICAL LASER PROBE

BACKGROUND

1. Technical Field

This application relates to a laser probe for use in ophthalmic procedures and more particularly to an anamorphic lens in a rotational scanning laser probe for use in ophthalmic diagnosis and therapy.

2. Description of Related Art

State-of-the-art laser ophthalmic therapies scan the retinal tissue with a surgical light or illumination beam. Imaging can be used to guide this scanning of the surgical light beam and to improve its precision. Typically, Optical Coherence Tomography (OCT) is used to image the target tissue, to perform diagnostics, and to combine diagnostics with therapeutic procedures that use a light beam. In an OCT procedure, a laser beam is directed at a spot of a target tissue. The OCT procedure collects data from a range of depths in an axial or A-scan. Data corresponding to different depth can be collected sequentially (time-domain OCT) or simultaneously (frequency domain OCT). Once the A-scan is completed, the beam can be redirected to a new spot where the A-scan is repeated. Scanning along a line of spots transverse to the optical axis of the system, the A-scans can be assembled into a 1+1 dimensional image, called a B-scan. If the spot is scanned along many lines or a line pattern covering an area, such as an X-Y pattern, a 2+1 dimensional image can be assembled, sometimes referred to as a C-scan. In many existing imaging systems the assembly of A-scans into B- or C-scans is simpler if the beam spot is scanned along straight lines.

In some ophthalmic therapies, the OCT imaging systems involve a cannula that is introduced into the eye with its end positioned proximal to the target tissue. The cannula carries inside an optical fiber to deliver an imaging light beam, and also has an optical head in the cannula or distal tip. The light beam is directed by the optical head from the cannula tip to the target tissue. The light beam is directed in a generally forward direction from the tip, forming a soft azimuthal angle (less than 90°) with a longitudinal axis of the cannula (LA). To reduce the invasiveness of the procedure, existing designs employ cannulas with a small outer diameter, for example in the 200-500 microns region. The small diameter of the cannula makes it a challenge to scan the imaging beam over a wide scanning pattern on the ophthalmic target such as over the retina.

Some typical choices of the scanning pattern include linear, raster and circular scanning patterns. The mechanical implementation of circular scanning can be easier and smoother than that of a linear or raster scanning, as a circular scanner can be operated continuously and smoothly to generate a periodic pattern, whereas a linear scanner has to be operated in a back-and-forth manner, resulting in vibrations, large accelerations and corresponding large forces, and thus in a faster rate of wear.

Remarkably, the advantageous linear scanning pattern, preferred because of the simplicity of the image assembly, can be generated by the advantageous circular scanning motion, preferred for its mechanical advantages. One design achieves this by employing two, counter-rotating optical elements, such as two prisms or faceted lenses in a so-called PARS design, as described, for example, in "Ex-vivo Optical Coherence Tomography Imaging of Schlemm Channels with a Scanning Endoscopic Probe," by Jian Ren, at IOVS, (Feb. 25, 2011).

The drawbacks of this PARS design include that, in order to obtain a linear scan, the two optical elements have to be synchronously rotated and counter-rotated about an axis of the device. The rotation of the two optical elements requires separate support systems for each, and the synchronization of the two rotations requires a complex gear mechanism. Obviously, the complexity of these three systems requires complex controls and also increases the likelihood of malfunction.

Furthermore, the moving elements in the cannula need to be contained in a non-moving exterior sheath to shield the tissue from abrasive contact with the moving parts of the cannula. The support systems, the gear system and the sheath all increase the diameter of the cannula, making the procedure undesirably invasive.

SUMMARY

In light of the above described disadvantages of the existing systems, there is a need for cannula assemblies that are (a) capable of transforming circular beam scanning or guiding motion into a linear scanning, but (b) use a smaller number of moving parts, (c) do not require the synchronous operation of gears and optical elements, and (d) have smaller diameters.

Embodiments of a surgical probe according to the present invention can satisfy at least some of these needs by including an outer cannula; an inner cannula, rotatably disposed inside the outer cannula; a rotational scanner, disposed at an end of the inner cannula and configured to receive a light beam from a delivery fiber and to scan the light beam along a loop; and an anamorphic optical element, disposed at an end of the outer cannula and configured to receive the light beam scanned along the loop and to output the light beam along an anisotropically compressed loop.

Some embodiments can include a method of scanning an imaging light beam by a surgical probe, the method comprising: providing a light beam by a light source to a delivery fiber; coupling the light beam from the delivery fiber to a rotational scanner at an end of an inner cannula; scanning the light beam by the rotational scanner along a loop; and receiving the light beam scanned along the loop by an anamorphic optical element and outputting the light beam along an anisotropically compressed loop to a target. These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Optical probes for ophthalmic procedures including Optical Coherence Tomography (OCT) imaging generally include a fiber-to-lens assembly generating a slowly converging beam with a small numerical aperture (NA) to form an elongated focus spot at an imaging distance from the tip of the probe. The imaging beam is typically directed to a surface point on the target tissue with the imaging distance placing the focus spot to a desired depth within the target tissue. The probe is configured to image the target in a range of depths corresponding to the surface point. This is often referred to as generating an A-scan. The A-scan can be generated either sequentially or synchronously. As described above, after the A-scan is completed, the beam can be moved to a subsequent point on the surface to generate a new A-scan. Generating a sequence of A-scans at a set of points along a line is referred to as a B-scan; along a raster pattern a C-scan.

To respond to the above described needs and challenges, embodiments of the present invention provide a cannula assembly that (a) is capable of transforming a rotational guiding or scanning motion into a linear scanning, (b) by using a smaller number of moving parts, (c) that do not require the synchronous operation of gears and optical elements, and (d) has a small diameter.

Embodiments disclosed herein may include a scanner with a single rotational element and an anamorphic optical element to linearly scan an imaging light beam on a target surface. The rotational scanner can be implemented as a rotating prism to refract or guide the imaging light beam along a circle or loop on a proximal surface of the anamorphic optical element. The anamorphic optical element may include two cylindrical surfaces having symmetry axes perpendicular to one another. The two cylindrical surfaces can be realized in two separate cylindrical lenses, or as two cylindrical surfaces of a single lens. Because of the orthogonally aligned cylindrical surfaces, the anamorphic optical element can strongly compress the circle or loop into an ellipse whose minor axis is much shorter than its major axis. The minor-to-major axis ratio, related to the aspect ratio of the ellipse, can be very small, making the ellipse appear as an approximately one-dimensional line or linear scan. The curvatures of the perpendicular cylindrical surfaces can determine the range or length of the linear scan.

Figure 1:
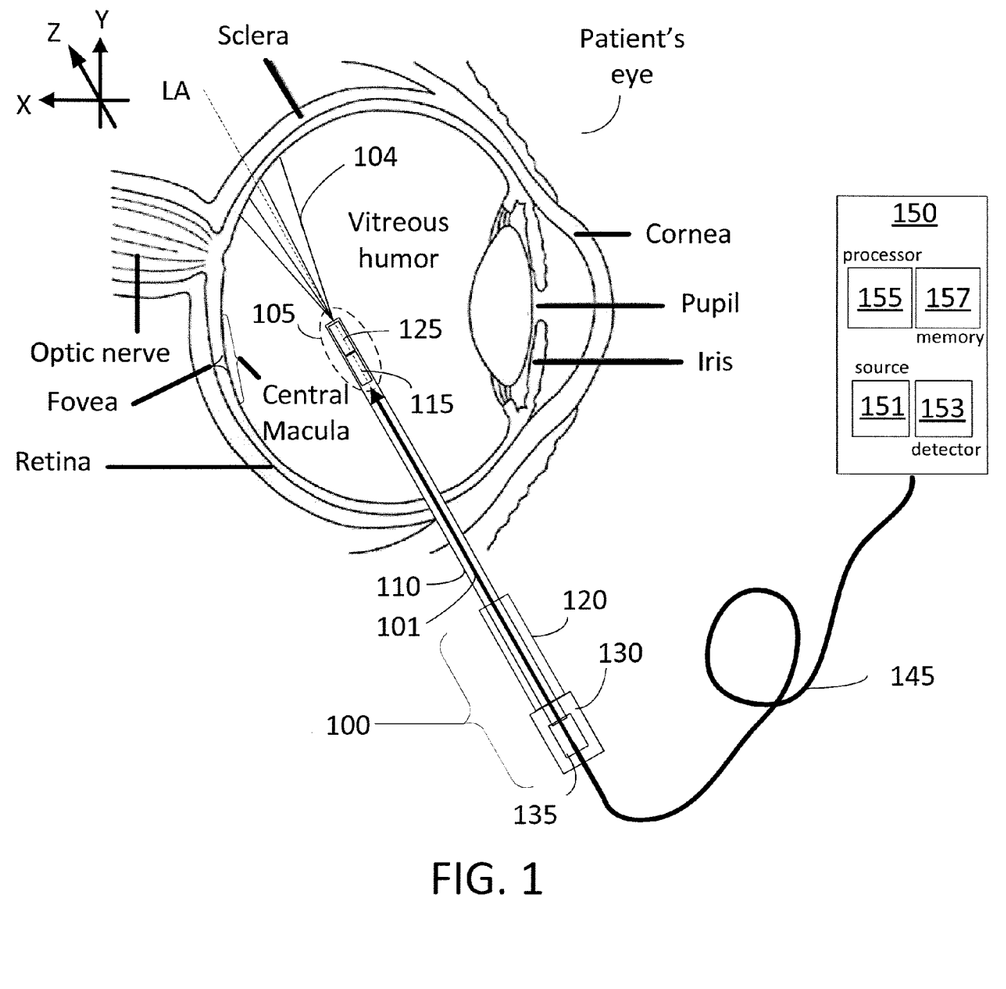
FIG. 1 shows a surgical probe adapted to form a linear scan of a laser beam for ophthalmic procedures, according to some embodiments.

FIG. 1 shows a surgical probe 100 adapted for ophthalmic imaging according to some embodiments. Surgical probe 100 can receive an illumination light from an optical cable 145 coupled to a control console 150. Using a processor circuit 155 and a memory circuit 157, control console 150 may be configured to control an ophthalmic procedure, performed with surgical probe 100. Control console 150 may include a light source 151 and a detector or imaging detector 153. Light source 151 and detector 153 may be coupled to optical cable 145 so that light source 151 can emit an imaging light beam towards a target tissue through the optical cable 145, and detector 153 can collect a returned light, guided by the optical cable 145 back from the imaged target tissue. Light source 151 may be a laser, a lamp, an arc lamp, or a light emitting diode (LED). In some embodiments, light source 150 may be a monochromatic light source such as a laser, or a broadband light source, such as an LED or an arc lamp. Further, according to some embodiments, light source 150 may include a continuum light source, a super-continuum light source, or a broadly tunable laser source. Moreover, in some embodiments light source 150 may be a continuous wave (CW) light source or a pulsed light source.

Processor circuit 155 may control the operation of light source 151 and detector 153 by executing commands stored in memory circuit 157 or inputted by a system operator. Moreover, console 150 may store data collected from detector 153 in memory circuit 157. Optical cable 145 may include an optical fiber bundle or a single optical fiber.

In an OCT procedure, an illumination light beam can be emitted from light source 151 to the target tissue through optical cable 145 and surgical probe 100. Probe 100 can be inserted in the patient's eye through an incision to guide the light beam received from optical fiber 145 through an optical head 105 onto the target tissue. A returned light from the target tissue can be guided back by probe 100 and optical cable 145 to detector 153 in console 150. Detector 153 can generate an interference from a reference light and the returned light in detector 153. The reference light is often generated from a portion of the imaging light. The interference can then be used to form an OCT image in control console 150, for example by processor 155 executing commands stored in memory circuit 157.

Surgical probe 100 may include a delivery fiber 101 inside a cannula assembly 110, a handling piece or handpiece 120, an adapter 130, and a motor 135. Motor 135 can be configured to rotate an inner cannula 210, as described in detail in relation to FIG. 2. Adapter 130 can couple the light beam received from optical cable 145 into delivery fiber 101. Adapter 130 may include optical elements to efficiently couple the light beam from optical cable 145 into delivery fiber 101. Delivery fiber 101 may be a single mode optical fiber, a multimode optical fiber, a fiber bundle, or a graded index (GRIN) optical fiber. Likewise, optical cable 145 may include a single mode optical fiber, a multimode optical fiber, a fiber bundle, or a combination of the above.

Cannula assembly 110 can include optical head 105 at the distal end. Optical head 105 can include a proximal rotational scanner 115 and a distal anamorphic optical element 125 to project or direct imaging light beam 104 toward the target tissue.

As shown in FIG. 1, in embodiments described hereinafter a 'proximal' element or portion refers to an element or portion that is closer to control console 150 along an optical path of the probe 100. Likewise, a 'distal' element or portion refers to an element or portion that is farther from the console 150 along the optical path, and thus closer to the target tissue.

FIG. 1 illustrates a three-dimensional (3D) XYZ Cartesian coordinate system, with its Z-axis oriented along the longitudinal axis (LA) or optical axis, in order to describe the orientation and operation of various elements of the embodiments. Obviously, there are many other possible orientations of the reference frame, all suitable for the description of the embodiments. With the present choice, the target tissue may be oriented substantially or approximately within an XY plane, perpendicular to the Z-axis, while imaging beam 104 may be directed substantially along the Z-axis or Z direction, substantially orthogonal to the XY plane. In some cases, the target tissue may make a large but less than 90 degree angle with the Z-axis.

In ophthalmic procedures using surgical probe 100, light beam or imaging beam 104 can be scanned along a scanning pattern that can be an anisotropically compressed loop, a line, or a two-dimensional pattern, to obtain an OCT image of the target tissue. In some embodiments, this scanning is achieved by cannula assembly 110 having moving components that adjust, refract, redirect or guide the direction of light beam 104 to follow the scanning pattern. Embodiments consistent with the present disclosure can achieve an essentially linear or strongly compressed loop scan by rotating only rotational scanner 115 without rotating anamorphic optical element 125, thus achieving some of the above described goals (a)-(d) as discussed in detail below in relation to FIG. 2.

Figure 2:
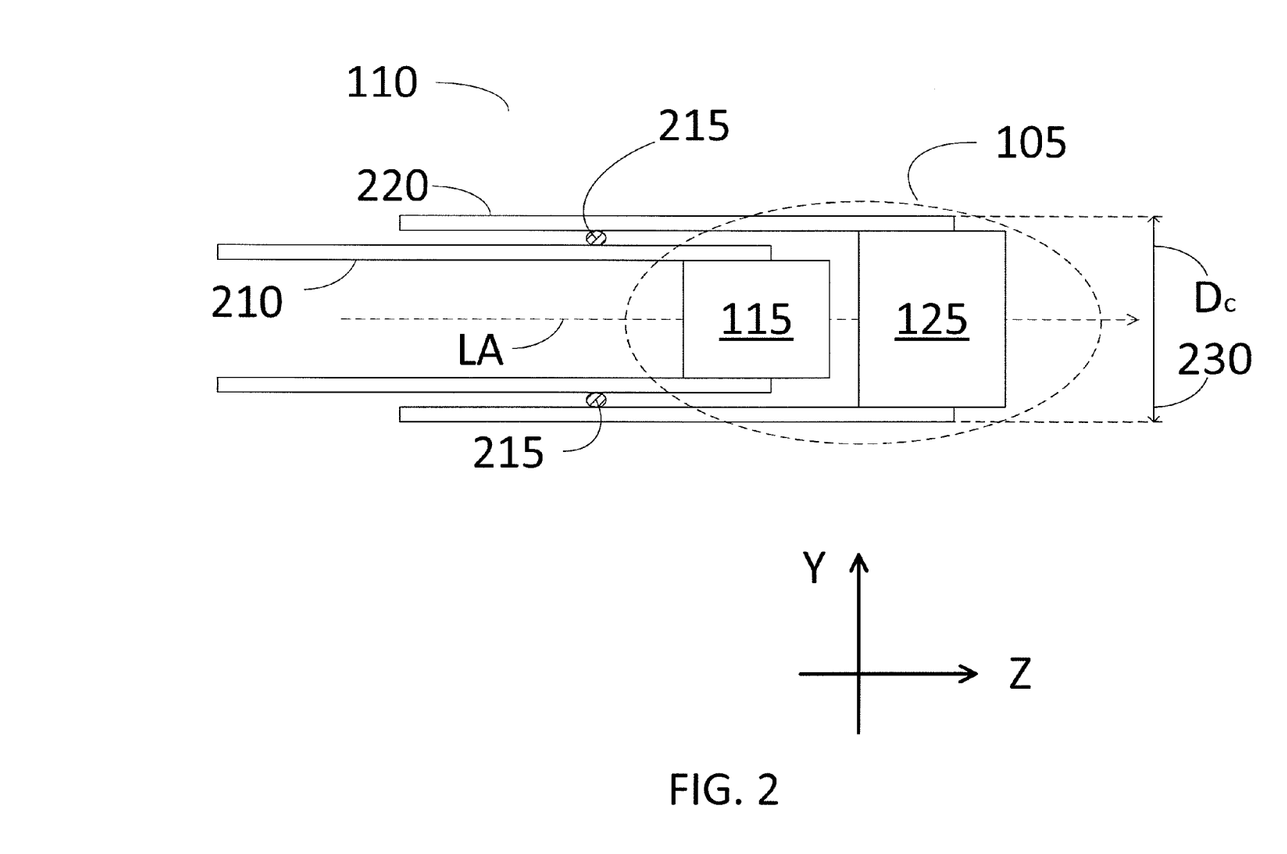
FIG. 2 shows an optical head in a cannula assembly, according to some embodiments.

FIG. 2 shows optical head 105 in cannula assembly 110, according to some embodiments. In some embodiments, cannula assembly 110 can include an outer cannula 220; an inner cannula 210, rotatably disposed inside outer cannula 220; rotational scanner 115, disposed at an end of inner cannula 210 and configured to receive a light beam from delivery fiber 101 and to scan the light beam along a loop; and anamorphic optical element 125, disposed at an end of outer cannula 220 and configured to receive the light beam scanned along the loop and to output the light beam along an anisotropically compressed loop.

In some embodiments, cannula assembly 110 can include bearings 215 to enable inner cannula 210 to rotate relative to outer cannula 220. In some embodiments, the imaging light beam can be scanned by rotating inner cannula 210 and rotational scanner 115 without rotating outer cannula 220 and anamorphic optical element 125. Outer cannula 220 may remain fixed during the rotation of inner cannula 210, thus eliminating the need for a rotating mechanism for outer cannula 220.

(a) In the above embodiments, probe 100 can scan the light beam along a loop by rotational scanner 115 towards anamorphic optical element 125 that can output an essentially linear scanning beam without rotating outer cannula 220. (b) Thus, probe 100 can use a smaller number of moving parts than the existing rotating-counter-rotating systems. (c) Further, probe 100 does not require the synchronous operation of gears and optical elements. (d) For all these reasons, probe 100 can have a smaller diameter and thus enable a less invasive ophthalmic procedure. Accordingly, in some embodiments the outer diameter Dc of the outer cannula 220 can be in the range of 100-800 microns, in others 200-500 microns.

Figure 3:
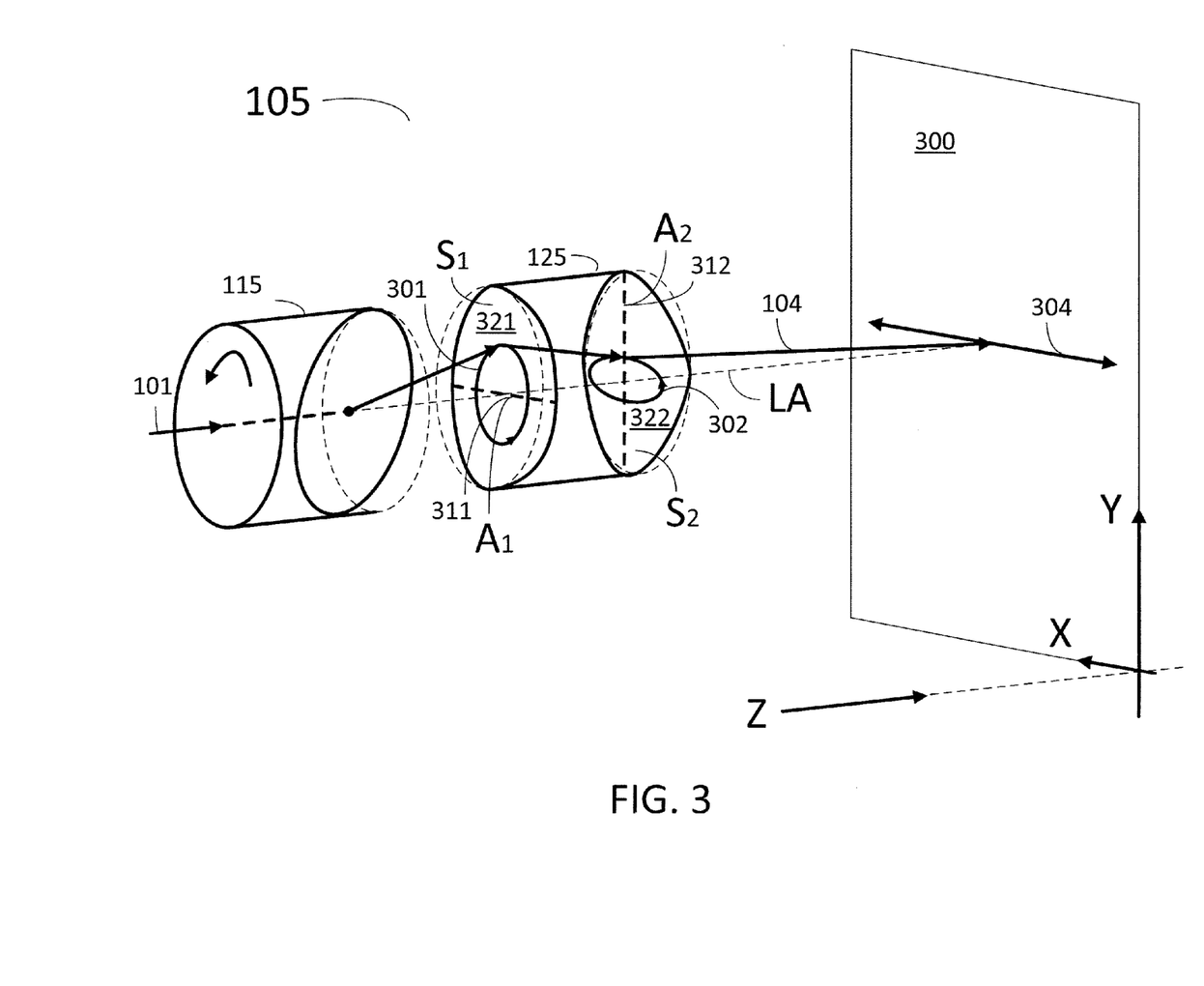
FIG. 3 shows optical elements in an optical head, according to some embodiments.

FIG. 3 shows rotational scanner 115 and anamorphic optical element 125 in optical head 105, according to some embodiments. Rotational scanner 115 can receive the imaging light beam from delivery fiber 101 through adapter 130 and refract, redirect or guide the light beam in a loop 301 to a first or proximal surface 321 ($S_1$) of anamorphic optical element 125. Anamorphic optical element 125 can be configured to transform loop 301 into a transformed loop 302 at its distal surface 322 ($S_2$). The light beam emitted according to transformed loop 302 from distal surface 322 ($S_2$) can appear as an anisotropically compressed loop 304 on the target surface 300 with an aspect ratio less than 1:10, in others, less than 1:50. This strongly anisotropic compression can make the loop 304 appear as an essentially linear scan 304 of light beam 104 on target surface 300.

In some embodiments, loop 301 may be generated by an anisotropic surface element of rotational scanner 115. Anisotropic surface element can be a wedge or a prism in order to deflect or refract the light beam 104 from delivery fiber 101 at an angle relative to the LA or Z-axis. In some embodiments, rotational scanner 115 can include a distal facet of a GRIN type lens, polished at an angle other than orthogonal relative to the Z-axis.

In some embodiments, rotational scanner 115 may include a lens or other optical element disposed off an optical axis or Z axis of the probe 100. Such a disposed or de-centered lens or optical element can cause a beam travelling along the LA or Z-axis to exit rotational scanner 115 at an angle different form zero, relative to the LA.

As described next in detail, in some embodiments anamorphic optical element 125 can be an anamorphic lens applying a scaling or magnification factor less than one in a first direction (e.g., Y-axis), and a scaling or magnification factor larger than one in a second direction perpendicular to the first direction (e.g., X-axis), while in other embodiments anamorphic optical element 125 can have two lenses, one applying a scaling factor in a first (Y) direction, the other lens applying a scaling factor larger than one in a second (X) direction.

In detail, in some embodiments, anamorphic optical element 125 may include proximal surface $S_1$ 321 and distal surface $S_2$ 322. For example, surface $S_1$ 321 may have a symmetry axis 311 ($A_1$) oriented parallel to the X-axis, and surface $S_2$ 322 may have a symmetry axis 312 ($A_2$) oriented parallel to the Y-axis. Thus, according to some embodiments, surface $S_1$ 321 may focus or de-focus the light beam in the Y-direction. Likewise, surface $S_2$ 322 may focus or de-focus the light beam in the X-direction.

While FIG. 3 shows anamorphic optical element 125 as a single optical element, some embodiments may include more than one optical element. For example, in some embodiments anamorphic optical element 125 may include a first cylindrical lens having surface $S_1$ 321, and a second cylindrical lens having surface $S_2$ 322.

In these embodiments, the net effect of anamorphic optical element 125 can be to provide an anisotropic scaling or magnification for loop 301. Such anisotropic scaling or magnification may include a scaling or magnification factor My in the Y-direction less than one (My<1). In some embodiments, My may be much lower than 1, such as 1/10, 1/20, 1/50, or even 1/100. The anisotropic scaling may also include a scaling factor in the X-direction larger than one: Mx>1. In some embodiments, the scaling factor in the X-direction may be much larger than 1, such as 10, 20, 50 or 100. The anisotropic scaling will be discussed in detail in relation to FIGS. 4A-B, below.

Figure 4A:
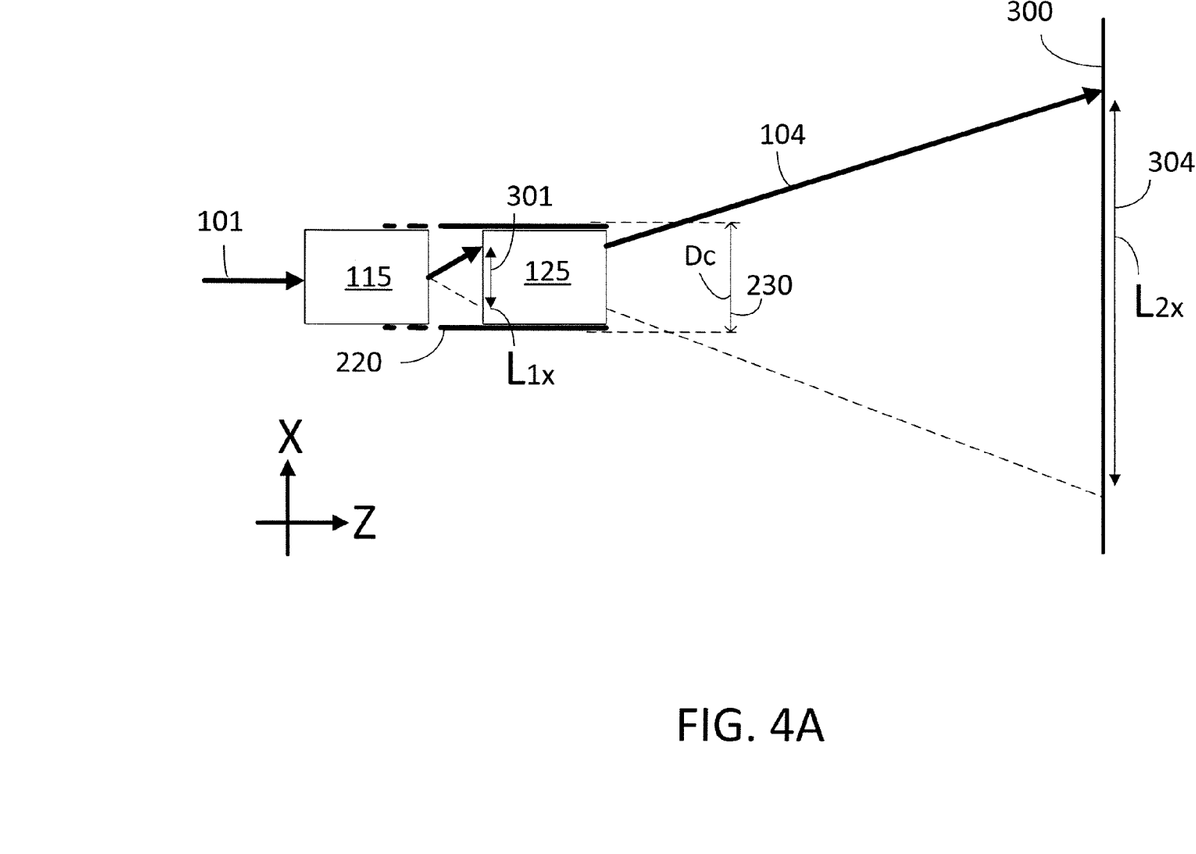
FIG. 4A shows a top view of optical elements in an optical head forming a scanning pattern, according to some embodiments.

FIG. 4A shows a top view of optical elements in an optical head forming a scanning pattern, according to some embodiments. In this schematic view in the XZ plane, trajectory or loop 301 may be a circle with a diameter L1x as rotational scanner 115 is rotated about the Z-axis or LA. Anamorphic optical element 125 can anisotropically scale light beam 104 to form anisotropically compressed loop or line 304 on target surface 300 with an extent L2x along the X axis on target surface 300. The scaling or magnification in the X-direction by anamorphic optical element 125 can be characterized by scaling or magnification factor Mx:

$$Mx = \frac{L2x}{L1x} \quad (1)$$

The value of Mx may be determined by the concavity or convexity of surface $S_1$ 321. In some embodiments, Mx can be greater than one. In some embodiments, surface $S_1$ 321 may have a strong concavity such that Mx>>1. For example, in some embodiments Mx may be 10, 20, 50, or 100.

Figure 4B:
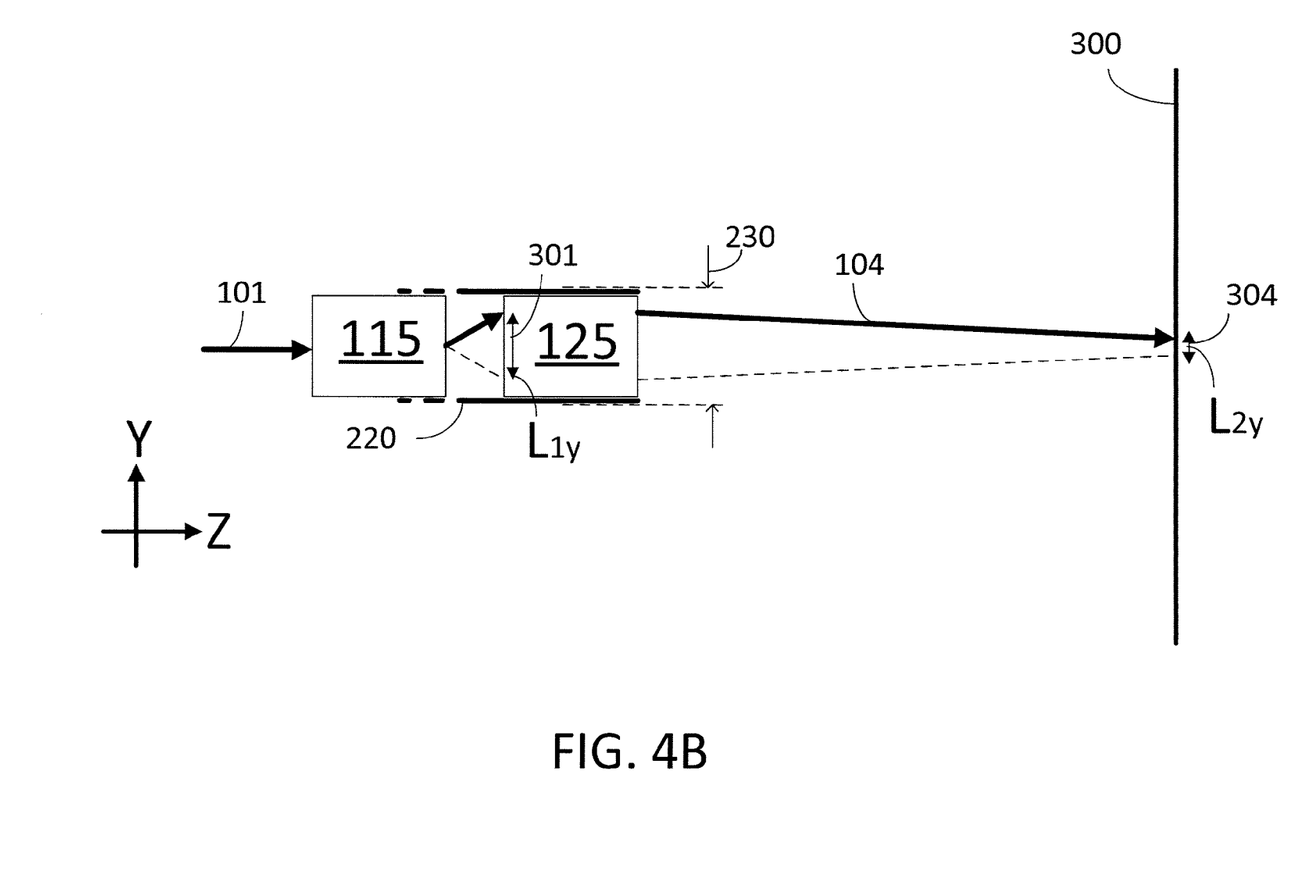
FIG. 4B shows a side view of optical elements in an optical head forming a scanning pattern, according to some embodiments.

FIG. 4B shows a side view of optical elements in optical head 105 forming a scanning pattern, according to some embodiments. In this schematic view in the YZ plane, trajectory or loop 301 may be a circle with a diameter L1y, as rotational scanner 115 is rotated about the Z-axis or LA. In the case of trajectory or loop 301 being a circle, L1y is equal to L1x. Anamorphic optical element 125 can refract, redirect or deflect light beam 104 to form anisotropically compressed loop 304 on target surface 300, such that anisotropically compressed loop 304 has a diameter L2y along the Y-axis on target surface 300. Anamorphic optical element 125 can scale or magnify loop 301 into anisotropically compressed loop 304 by the scaling or magnification factor My along the Y direction:

$$My = \frac{L2y}{L1y} \quad (2)$$

The value of My may be determined by the concavity or convexity of surface $S_2$ 322. In some embodiments, My can be less than one. In some embodiments, surface $S_2$ 322 may have a concavity such that My<<1. For example, in some embodiments My may be less than 1/10, 1/20, 1/50 or 1/100.

In general, anisotropically compressed loop 304 is an elongated ellipse, with a high degree of eccentricity, or highly anisotropic aspect ratio. In terms of the scaling or magnification ratios, in embodiments the ratio of the scaling factors, Mx/My can be larger than 10, 20, 50 or 100.

In some embodiments, L2y may be comparable to or smaller than a spot size of light beam 104 on target surface 300, thus making anisotropically compressed loop 304 substantially a line or linear scan.

While FIGS. 4A-B show a specific choice of scaling factors such that My<Mx, or My<<Mx, one of ordinary skill may recognize that this relation depends on the choice of the orientation of the coordinate axes X and Y. In general, embodiments consistent with the present disclosure may have scaling factors Mx and My with Mx<1<My.

Figure 5A:
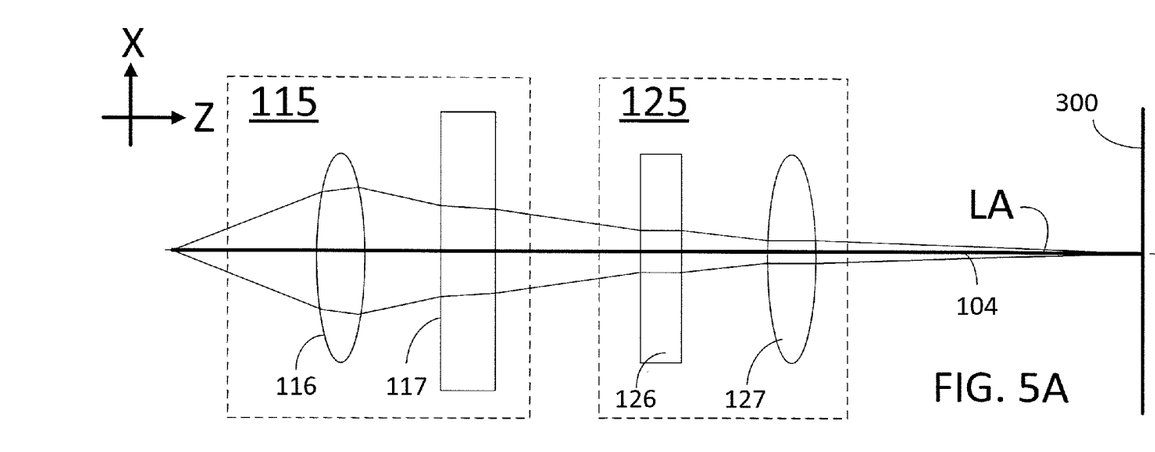
FIG. 5A shows a top view of optical elements in an optical head directing a beam onto a target surface, according to some embodiments.
Figure 5B:
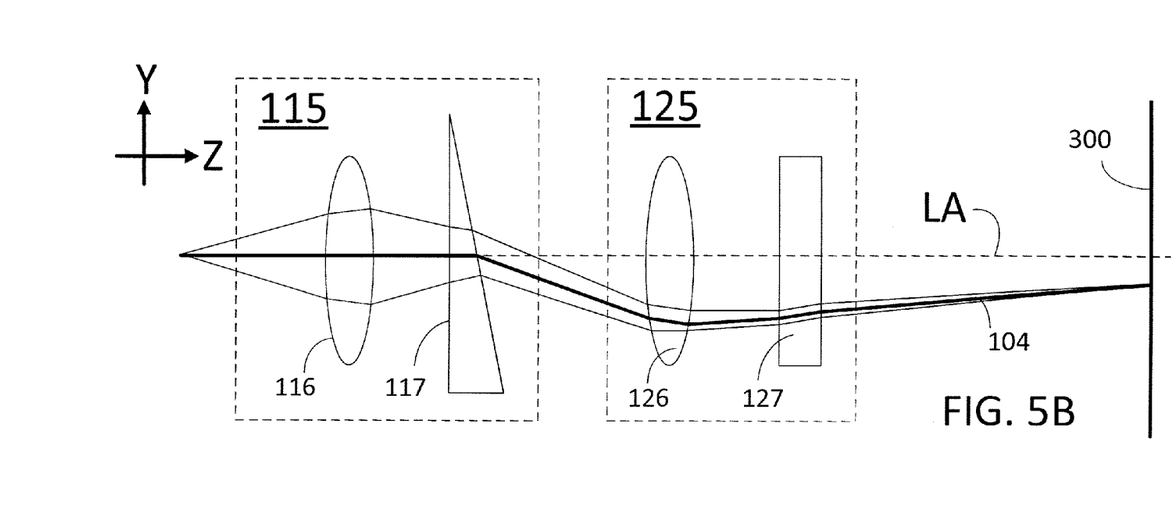
FIG. 5B shows a side view of optical elements in an optical head directing a beam onto a target surface, according to some embodiments.

FIGS. 5A-B show two orthogonal side views of optical head 105 in a specific configuration. FIG. 5A shows a side view in the XZ plane and FIG. 5B shows a side view in the YZ plane.

FIG. 5A shows a top view of optical elements 115 and 125 in optical head 105 directing light beam 104 onto target surface 300, according to some embodiments. Rotational scanner 115 may include a lens 116 and a wedge prism 117. In some embodiments, lens 116 and wedge prism 117 may be coupled so that when element 115 is rotated about the LA, lens 116 and wedge prism 117 rotate together.

Anamorphic optical element 125 may include a first optical element, such as a first cylindrical lens 126, and a second optical element or second cylindrical lens 127. First cylindrical lens 126 may have a cylindrical symmetry axis along the X-axis, and second cylindrical lens 127 may have a cylindrical symmetry axis along the Y-axis.

In embodiments consistent with the present disclosure, diameters L1x and L1y of loop 301 can be determined by the distance between elements 117 and 126 and by the wedge angle of prism 117. The focusing power of lens 116 may be adjusted to focus light beam 104 to an imaging distance that can be on target surface 300 or beyond it to image the target in depth.

Figure 5C:
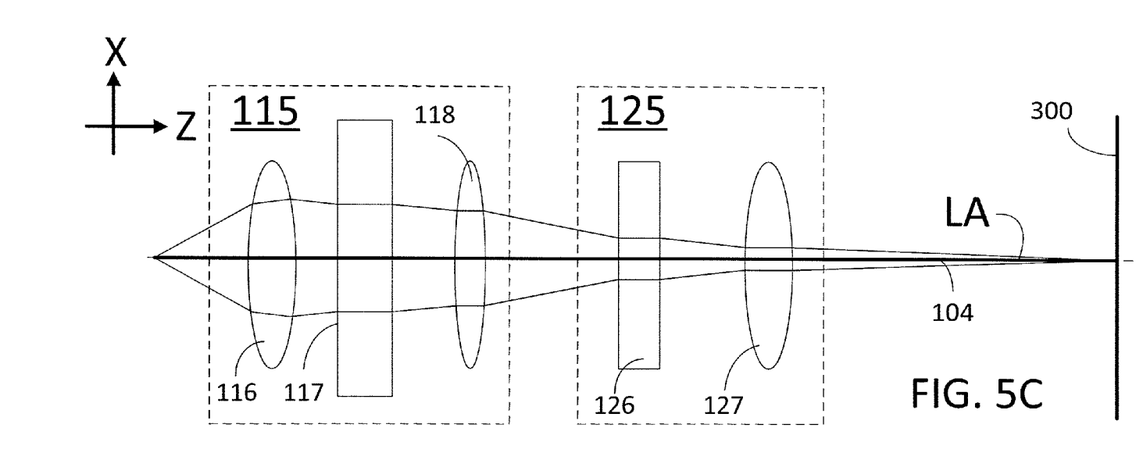
FIG. 5C shows a top view of optical elements in an optical head directing a beam onto a target surface, according to some embodiments.
Figure 5D:
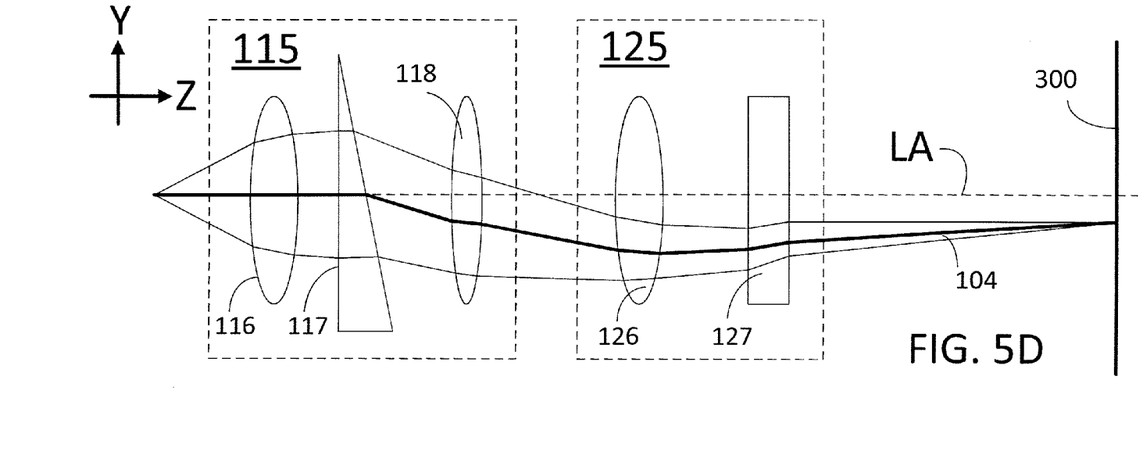
FIG. 5D shows a side view of optical elements in an optical head directing a beam onto a target surface, according to some embodiments.

FIGS. 5C-D show two orthogonal views of optical head 105 in another specific configuration. Optical head 105 may include similar elements as those shown in FIGS. 5A-B, with rotational scanner 115 additionally including lens 118. Lens 118 may be positioned distal to wedge prism 117. Some embodiments may include lens 118 having axial symmetry about the Z-axis or LA to provide an additional degree of freedom for controlling the size and shape of scan pattern 304. By adjusting the focusing power of lens 118, diameter L1x (and L1y) of loop 301 may be adjusted. Furthermore, adjusting the focusing power of lens 118 may adjust the numerical aperture of input and output rays for anamorphic optical element 125. Thus, scaling factors Mx and My may also be adjusted with lens 118. In some embodiments, lens 118 can be positioned off-axis, providing additional rotational scanner functionality. Finally, in some embodiments lens 118 may be coupled to lens 116 and wedge prism 117 in rotational scanner 115. Thus, lens 118 may rotate together with lens 116 and wedge prism 117.

Figure 6:
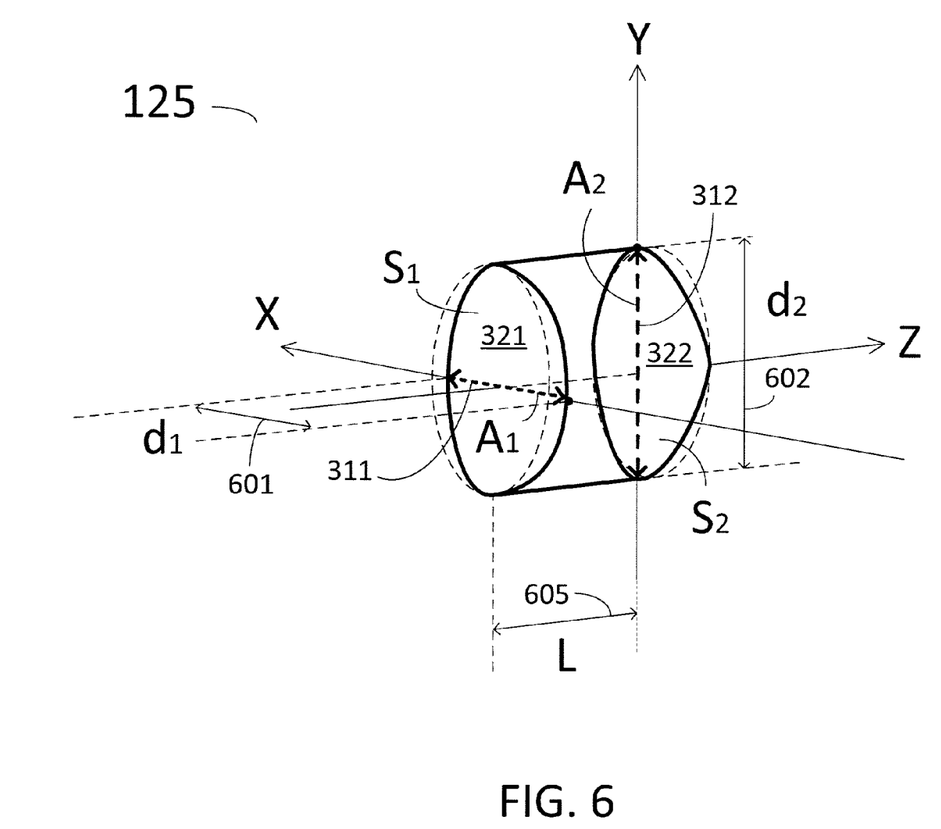
FIG. 6 shows an anamorphic optical element for an optical head, according to some embodiments.

FIG. 6 shows an embodiment of anamorphic optical element 125 according to some embodiments, such as shown in FIG. 3. As before, surfaces $S_1$ and $S_2$ may be cylindrical surfaces disposed such that the symmetry axis 311 ($A_1$) of surface $S_1$ is perpendicular to the symmetry axis 312 ($A_2$) of surface $S_2$. For example, in FIG. 6 axis $A_1$ is parallel to the X-axis, and axis $A_2$ is parallel to the Y-axis. In the embodiment of FIG. 6 anamorphic optical element 125 has a diameter 601 ($d_1$) in the X-direction and a diameter 602 ($d_2$) in the Y-direction. According to some embodiments, $d_1$ can be essentially equal to $d_2$, so that anamorphic element 125 may fit in cylindrical outer cannula 220 of FIG. 2. A length L of anamorphic element 125 along the Z-axis can be length 605.

A desirable feature of anamorphic optical element 125 as shown in FIG. 6 is that a single optical element may provide anisotropic scaling in both X and Y directions: Mx≠My. This reduces the assembly complexity, since alignment between surfaces $S_1$ and $S_2$ is provided in a single optical element. Moreover, having a single optical element allows a substantial reduction of length L 605.

Surface $S_1$ 321 can have a curvature that, combined with the refractive index of the material used in anamorphic element 125 and the focusing power of the one or two lenses 116/118 in rotational scanner 115 determine the scaling factor My of optical head 105. Likewise, the curvature of surface $S_2$ 322, combined with the refractive index of the material used in anamorphic element 125 and the focusing power of the one or two lenses 116/118 in rotational scanner 115 determine the scaling factor Mx of optical head 105.

Figure 7:
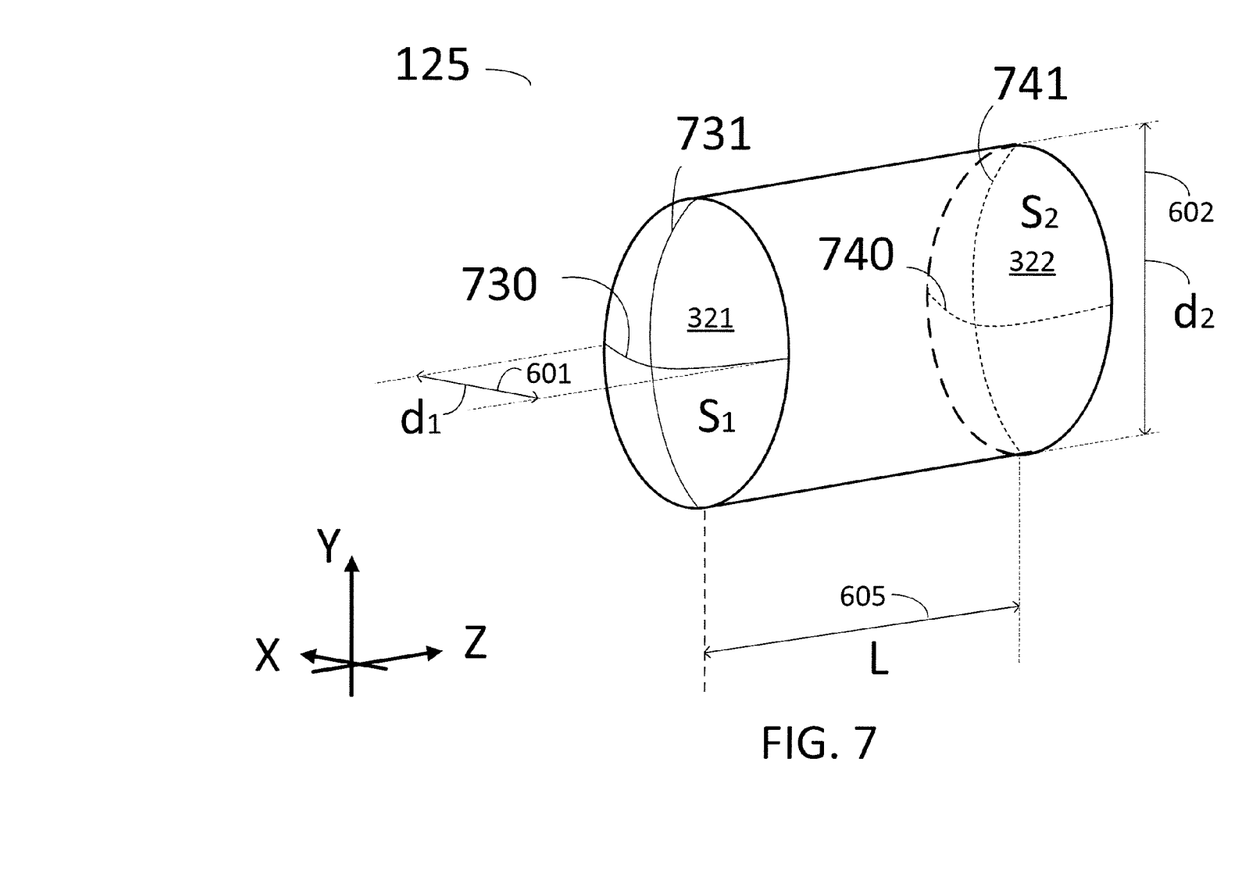
FIG. 7 shows an anamorphic optical element for an optical head, according to some embodiments.

FIG. 7 shows anamorphic optical element 125 for optical head 105 according to some embodiments. Anamorphic optical element 125 may be formed as a single optical element, similarly to FIG. 6, having first surface $S_1$ 321 and second surface $S_2$ 322. As a generalization of the previous embodiments, surface $S_1$ 321 may have a first curvature 730 along the X-direction and a second curvature 731 along the Y-direction. Likewise, surface $S_2$ 322 may have a first curvature 740 along the X-direction and a second curvature 741 along the Y-direction.

In this generalized embodiment of anamorphic optical element 125 each anisotropic scaling factor Mx and My is impacted by both surfaces, thus providing larger flexibility for the system design, and the possibility of improving the system performance in other aspects, like astigmatism. A desired scaling factor Mx may be obtained by selecting curvatures 730 and 740, and the material element 125 is made of. Likewise, a desired scaling factor My may be obtained by selecting curvatures 731 and 741, and the material of element 125. Curvatures 731 and 741 can be selected independently of curvatures 730 and 740. Embodiments consistent with the present disclosure may use materials and optical properties of rotational scanner 115 independently from materials and optical properties of anamorphic optical element 125. For example, curvatures 730, 731, 740 and 741, may be chosen independently of the focusing power of lens 116, the distance between lens 116 and wedge prism 117, and the wedge angle in wedge prism 117.

As described before, surgical probe 100 can include optical cable 145, configured to deliver light beam 104 from light source 151 to probe 100, and adapter 130, configured to receive light beam 104 from optical cable 145 and to couple the received light beam into delivery fiber 101.

Surgical probe 100 can also include handpiece 120 to partially encase outer cannula 220; and motor 135 to rotate inner cannula 210. Surgical probe 100 can also be a part of an Optical Coherence Tomography (OCT) imaging system, where the OCT imaging system includes light source 151, configured to emit light beam 104 into optical cable 145 toward surgical probe 100; imaging detector 153, configured to receive a returned imaging beam from surgical probe 100 through optical cable 145 and to create an interference from the returned imaging beam and a reference beam; and imaging processor 155, configured to generate an image from the interference.

Figure 8:
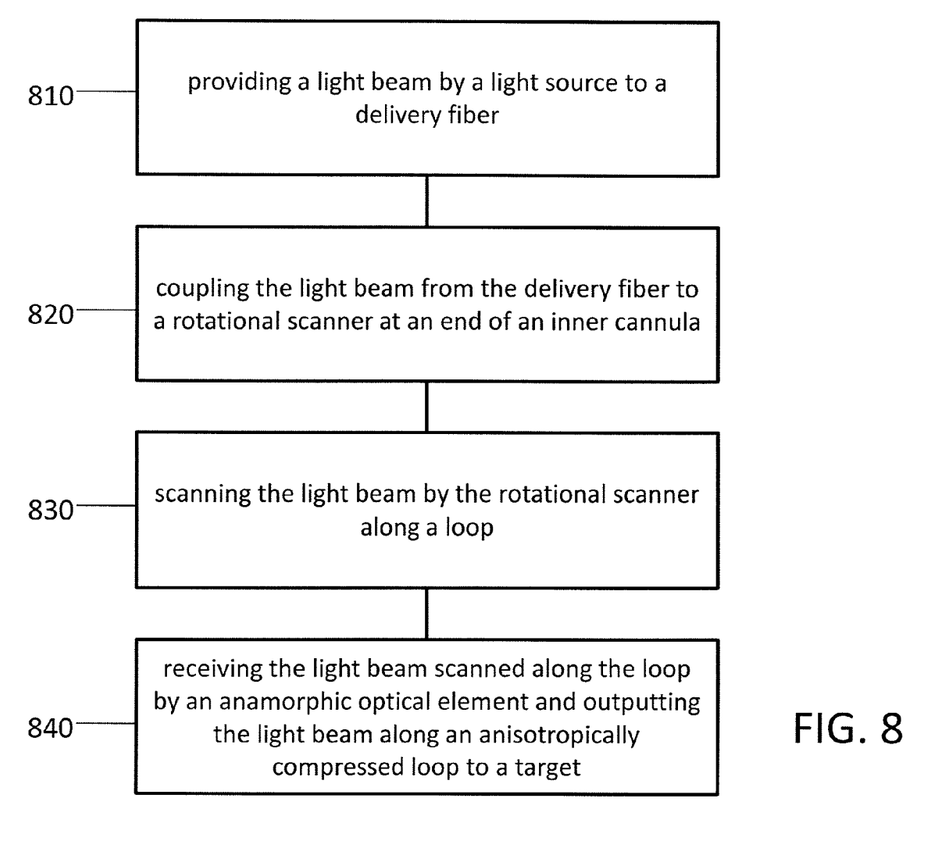
FIG. 8 shows a flow chart in a method to form a scanning pattern, according to some embodiments.

FIG. 8 shows a flow chart of a method 800 of scanning an imaging light beam by a surgical probe, such as surgical probe 100. Step 810 can include providing a light beam by a light source to a delivery fiber, such as providing light beam 104 by light source 151 to delivery fiber 101. Step 820 can include coupling the light beam from the delivery fiber to a rotational scanner at an end of an inner cannula, such as coupling light beam 104 from delivery fiber 101 to rotational scanner 115 at an end of inner cannula 220. Step 830 can include scanning the light beam by the rotational scanner along a loop, such as scanning light beam 104 by rotational scanner 115 along loop 301. Finally, step 840 can include receiving the light beam scanned along the loop by an anamorphic optical element and outputting the light beam along an anisotropically compressed loop to a target, such as receiving light beam 104 scanned along the loop 301 by anamorphic optical element 125 and outputting light beam 104 along an anisotropically compressed 304 loop to a target. In some embodiments, the anisotropically compressed loop can be a line. The details of this method can proceed analogously to the operation of surgical probe 100 provided above in relation to FIGS. 1-7.

Some embodiments of the method can include receiving a returned light from the target by surgical probe 100, the returned light travelling in opposite direction to the light beam; interfering the returned light and a reference light by an image detector 153; and generating an image from the interfered light by an image processor 155. These steps can be part of forming an OCT image of the target. The OCT image can be an A-scan, B-scan or C-scan, as detailed above.

In some embodiments, steps of method 800 may be performed by a control console coupled to a surgical probe, such as control console 150 and surgical probe 100 in FIG. 1. Control console may include a processor circuit and a memory circuit (e.g., processor circuit 155 and memory circuit 157). The processor circuit in the control console may execute operations upon receiving commands stored in the memory circuit, thus performing at least some steps in method 800. In some embodiments, steps in method 800 may be partially performed by an operator handling the surgical probe, directing the probe onto a target tissue. For example, an operator may use a handling piece to manipulate the surgical probe (e.g., handpiece 120 in FIG. 1). The handling piece in the surgical probe may include a button or a plurality of buttons, coupled to electrically operate some of the components in the surgical probe. For example, a manually operated button may start a rotational motion of an optical element in the surgical probe. In some embodiments, an operator actuated button in the handling piece may turn on a light source coupled to the surgical probe (e.g., light source 151, cf. FIG. 1).

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

The invention claimed is:

1. A surgical probe, comprising:
a fixed outer cannula;
an inner cannula disposed inside the fixed outer cannula and operable to rotate relative to the fixed outer cannula;
a rotational scanner coupled to an end of the inner cannula, the rotational scanner configured to receive a light beam from a delivery fiber and to focus the light beam along the path of a loop as the rotational scanner rotates due to the rotation of the inner cannula; and
an anamorphic optical element coupled to an end of the fixed outer cannula and configured to receive the light beam focused along the path of the loop by the rotational scanner and to further focus the light beam along an anisotropically compressed loop falling in a plane distal to a distal most end of the surgical probe, the anamorphic optical element comprising:
a first optical element with a surface having a first symmetry axis perpendicular to an optical axis of the probe; and
a second optical element with a surface having a second symmetry axis perpendicular to the first symmetry axis and to the optical axis of the probe.

2. The surgical probe of claim 1 wherein:
the rotational scanner comprises at least one of a wedge, a wedged prism, and a GRIN lens with an angled distal surface.

3. The surgical probe of claim 1 wherein:
the rotational scanner comprises an optical element disposed off an optical axis of the probe.

4. The surgical probe of claim 1 wherein:
the rotational scanner is rotatable by a rotation mechanism without rotating the anamorphic optical element.

5. The surgical probe of claim 1, wherein:
the first optical element is a first cylindrical lens with the first symmetry axis; and the second optical element is a second cylindrical lens with the second symmetry axis.

6. The surgical probe of claim 1, wherein:
the anisotropically compressed loop is scaled in a first direction by a first scaling factor and in a second direction by a second scaling factor, wherein
a ratio of the first scaling factor and the second scaling factor is larger than 10.

7. The surgical probe of claim 1, wherein:
the anisotropically compressed loop is a line.

8. The surgical probe of claim 1, comprising:
an optical cable, configured to deliver the light beam from a light source to the probe; and
an adapter, configured to receive the light beam from the optical cable, and to couple the received light beam into the delivery fiber.

9. The surgical probe of claim 1, comprising:
a handpiece to partially encase the outer cannula; and
a motor to rotate the inner cannula.

10. The surgical probe of claim 1, wherein:
the surgical probe is part of an Optical Coherence Tomography (OCT) imaging system, the OCT imaging system comprising
a light source, configured to emit the light beam into an optical cable toward the surgical probe;
an imaging detector, configured to receive a returned imaging beam from the surgical probe through the optical cable and to create an interference from the returned imaging beam and a reference beam; and
an imaging processor, configured to generate an image from the interference.

11. A surgical probe, comprising:
a fixed outer cannula;
an inner cannula disposed inside the fixed outer cannula and operable to rotate relative to the fixed outer cannula;
a rotational scanner coupled to an end of the inner cannula, the rotational scanner configured to receive a light beam from a delivery fiber and to focus the light beam along the path of a loop as the rotational scanner rotates due to the rotation of the inner cannula; and
an anamorphic optical element coupled to an end of the fixed outer cannula and configured to receive the light beam focused along the path of the loop by the rotational scanner and to further focus the light beam along an anisotropically compressed loop falling in a plane distal to a distal most end of the surgical probe, the anamorphic optical element comprising:
a proximal surface having a first proximal curvature in a first proximal direction and a second proximal curvature in a second proximal direction; and
a distal surface having a first distal curvature in a first distal direction and a second distal curvature in a second distal direction.

12. The surgical probe of claim 11 wherein:
the rotational scanner comprises at least one of a wedge, a wedged prism, and a GRIN lens with an angled distal surface.

13. The surgical probe of claim 11 wherein:
the rotational scanner comprises an optical element disposed off an optical axis of the probe.

14. The surgical probe of claim 11 wherein:
the rotational scanner is rotatable by a rotation mechanism without rotating the anamorphic optical element.

15. The surgical probe of claim 11, wherein:
the anisotropically compressed loop is scaled in a first direction by a first scaling factor and in a second direction by a second scaling factor, wherein
a ratio of the first scaling factor and the second scaling factor is larger than 10.

16. The surgical probe of claim 11, wherein:
the anisotropically compressed loop is a line.

17. The surgical probe of claim 11, wherein:
the surgical probe is part of an Optical Coherence Tomography (OCT) imaging system, the OCT imaging system comprising
a light source, configured to emit the light beam into an optical cable toward the surgical probe;
an imaging detector, configured to receive a returned imaging beam from the surgical probe through the optical cable and to create an interference from the returned imaging beam and a reference beam; and
an imaging processor, configured to generate an image from the interference.

* * * * *